(12) United States Patent
Smith et al.

(10) Patent No.: US 6,666,825 B2
(45) Date of Patent: Dec. 23, 2003

(54) ULTRASOUND TRANSDUCER FOR IMPROVING RESOLUTION IN IMAGING SYSTEM

(75) Inventors: Lowell Scott Smith, Niskayuna, NY (US); Nim Hak Tea, Los Angeles, CA (US); Theodore Lauer Rhyne, Whitefish Bay, WI (US); Xuan-Ming Lu, San Jose, CA (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/898,811

(22) Filed: Jul. 5, 2001

(65) Prior Publication Data

US 2003/0032884 A1 Feb. 13, 2003

(51) Int. Cl.$^7$ ................................................. A61B 8/00
(52) U.S. Cl. ........................ 600/459; 600/443; 29/25.35
(58) Field of Search ................................ 600/437, 443, 600/447, 459; 73/625–626, 631; 29/25.35; 310/334–336

(56) References Cited

U.S. PATENT DOCUMENTS 5,553,035 A * 9/1996 Seyed-Bolorforosh et al. .. 367/140
5,706,564 A   1/1998 Rhyne
5,886,250 A * 3/1999 Greenwood et al. ........ 73/32 A
6,049,159 A * 4/2000 Barthe et al. ................ 310/334

OTHER PUBLICATIONS

"Computer Optimization of Transducer Transfer Functions Using Constraints on Bandwidth, Ripple, and Loss," Theodore L. Rhyne, IEEE Transactions on Ultrasonics,Ferroelectrics,a nd Frequency Control, vol. 43, No. 6, Nov. 1996, pp. 1136–1149.
"Characteristics of Relaxor–Based Piezoelectric Single Crystals for Ultrasonic Transducers," Seung–Eek Park; Thomas R. Shrout, IEEE Ultrasonics Symposium, 1996, pp. 935–942.
"The Role of Piezocomposites in Ultrasonic Transducers," Wallace Arden Smith, IEEE Ultrasonics Symposium, 1989, pp. 755–766.
"Acoustic Fields and Waves in Solids," B.A. Auld, vol. 1, pp. 73–87.

* cited by examiner

Primary Examiner—Francis J. Jaworski
(74) Attorney, Agent, or Firm—Jean K. Testa; Patrick K. Patnode

(57) ABSTRACT

An ultrasound transducer employs a silicon acoustic matching layer closest to the piezoelectric layer in order to achieve improved resolution. A silicon wafer, ground to an appropriate thickness, is included in the acoustic stack with other matching layer materials during transducer construction. The exact thickness is determined by the details of the design, but is nominally a quarter wavelength in the silicon.

25 Claims, 4 Drawing Sheets

ULTRASOUND TRANSDUCER FOR IMPROVING RESOLUTION IN IMAGING SYSTEM

BACKGROUND OF THE INVENTION

This invention relates generally to ultrasound imaging systems and, more particularly, to an ultrasound transducer design that improves the resolution of an ultrasound imaging system.

Ultrasound transducers used for medical imaging and non-destructive testing are characterized by two main properties, sensitivity and bandwidth, which are directly correlated to the penetration and resolution of the imaging system. As transducer designs have become more sophisticated, fractional bandwidth has increased from 30–40% with a single matching layer to 60–80% with two matching layers. In medical diagnostic ultrasound imaging, recent advances in harmonic imaging, with and without contrast agents, have highlighted the benefits of even broader bandwidth probes. As implied by the name, harmonic imaging requires sensitivity at over 100% fractional bandwidth. The fractional bandwidth (FBW) is defined as the bandwidth divided by the center frequency:

$$FBW = \frac{U_{lim} - L_{lim}}{f_{ctr}}$$

where $U_{lim}$ is the upper limit of the bandwidth, $L_{lim}$ is the lower limit of the bandwidth, and $f_{ctr}$ is the center frequency.

A very-wide-bandwidth probe can simplify scanning by reducing the number of probes needed to perform a diagnosis. In conventional situations, a high-frequency probe is needed to look for fine detail close to the skin and a lower-frequency probe is used for color flow imaging, Doppler imaging, and imaging at greater depths in the body. It takes time and operator motions to switch between probes. If this can be minimized, the time and effort required to complete a patient scan can be reduced.

Efficient ultrasound transducers have a very different acoustic impedance than most objects under test. This makes it difficult to couple ultrasound waves between these two materials. It is well known that acoustic matching layers improve the sensitivity and bandwidth of ultrasound transducers by more efficiently transmitting acoustic energy from materials of one specific acoustic impedance, such as piezoelectric ceramics, to materials of a different specific acoustic impedance, such as water baths or the human body.

The theory of acoustic matching layers is well understood and is very similar to electronic filter design methods, as disclosed by T. Rhyne in "Computer Optiaebzation of Transducer Transfer Functions Using Constraints on Bandwidth, Ripple, and Loss," *IEEE Trans. Ultrasonics, Ferroelectrics, and Frequency Control*, Vol. 43, No. 6, pp. 1136–1149 (November 1996). By adjusting the acoustic impedance and thickness of the matching layers, a variety of standard bandpass characteristics can be achieved, as disclosed in U.S. Pat. No. 5,706,564 to Rhyne. As shown in the Rhyne patent, a convenient continuum exists between the Thompson and Butterworth band shapes. The practical difficulty for ultrasound transducers is that the optimal acoustic impedances for many matching layers are not attainable with simple materials. For example, in two-layer designs the inner matching layer needs to have an impedance of about 7–10 Mrayls. This is inconveniently higher than plastics (2–4 Mrayls) and less than glasses and metals (10–100 Mrayls).

When trying to increase ultrasound transducer bandwidth, several approaches are possible. However, many involve complicated material developments such as the growth of large single-crystal piezoelectrics, or complex composite structures. See, for example, Park et al., "Characteristics of Relaxor-Based Piezoelectric Single Crystals for Ultrasonic Transducers," 1996 *IEEE Ultrasonics Symposium*, pp. 935–942 (1996), and W. A. Smith, "The Role of Piezocomposites in Ultrasound Transducers," 1989 *IEEE Ultrasonics Symposium*, pp. 755–766 (1989). Thus there is need for a simple matching layer material having optimal acoustic impedance and which can be easily processed.

BRIEF SUMMARY OF THE INVENTION

An ultrasound transducer achieves significantly better resolution by fabricating the acoustic matching layer closest to the piezoelectric layer from silicon. Silicon is a simple, ubiquitous and readily available material which has been extensively studied, is inexpensive, and is relatively easy to process. Since silicon is the building block for essentially all semiconductor electronics, wafers up to many inches in diameter are readily available.

In the simplest embodiment, a silicon wafer as obtained for semiconductor processing is ground to an appropriate thickness, and included in the acoustic stack with other matching layer materials during transducer construction. The exact thickness is determined by the details of the design, but is nominally a quarter wavelength in the material.

In accordance with one preferred embodiment, the transducer matching layer structure is designed (using computer optimization) to produce a Chebyshev bandshape. For this bandshape, the ideal acoustic impedance for the third layer is about 18.6 Mrayls, so that the standard silicon wafer having an acoustic impedance of 19.6 Mrayls is nearly, but not quite, optimum. However, different shapes lead to modified values of the acoustic impedance. By changing the shape of the silicon to a narrow beam, for example, which is the appropriate shape for a transducer array element, a better match to the desired impedance is obtained.

In a further embodiment, the silicon wafer orientation can be selected to more accurately match the silicon acoustic impedance to that required for a specific bandshape design. Since silicon is a cubic material, three standard orientations or "cuts" designated by Miller indices (100), (110) and (111) are available. These indices are related to the orientation of the wafer plane relative to the crystal axes. In a more complex preferred embodiment, if alternative cuts are taken, even more flexibility in acoustic impedance is possible.

DETAILED DESCRIPTION OF THE INVENTION

Figure 1:
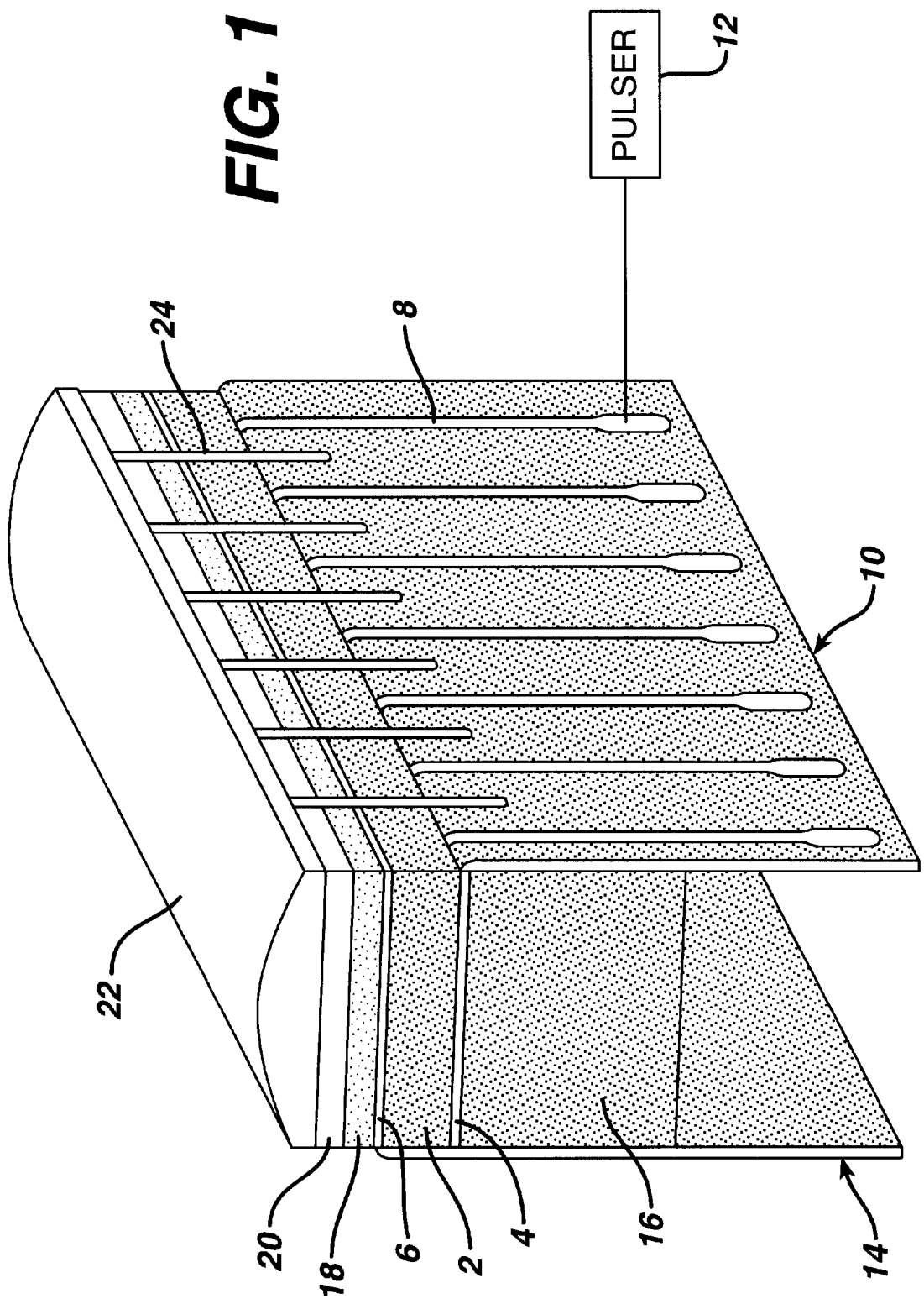
FIG. 1 is an isometric illustration view of a conventional transducer pallet.

A conventional ultrasonic probe comprises a transducer pallet which must be supported within a probe housing. As shown in FIG. 1, a conventional transducer pallet comprises a linear array of narrow transducer elements. Each transducer element comprises a layer 2 of piezoelectric ceramic material. The piezoelectric material is typically a ceramic, such as lead zirconate titanate (PZT) difluoride or PZT ceramic/polymer composite.

Typically, the piezoelectric material 2 of each transducer element has a signal electrode 4 on its rear face and a ground electrode 6 on its forward face. Each signal electrode 4 can be connected to a signal source, e.g., a respective pulser 12 in the transmitter (not shown) of the ultrasound imaging system to which the probe is connected via a respective conductive trace 8 on a signal flexible printed circuit board (PCB) 10. Each signal electrode typically is also selectively connectable to a respective receiver channel (not shown). The amplitude, timing and transmit sequence of the transmit pulses applied by the pulsers are determined by various control means incorporated in the system transmitter. Each ground electrode 6 is connected to a common ground (not shown) via a respective trace (not shown) on a ground flexible PCB 14. Preferably both flexible PCBs are on the same side of the pallet although in FIG. 1 they are shown on opposite sides of the pallet for simplicity of illustration only.

The transducer pallet also comprises a mass 16 of suitable acoustical damping material having high acoustic losses, e.g., metal-loaded epoxy, positioned at the back surface of the transducer element array. This backing layer 16 is coupled to the rear surface of the transducer elements to absorb ultrasonic waves that emerge from the back side of each element, so that they will not be partially reflected and interfere with the ultrasonic waves propagating in the forward direction.

Typically, each transducer array element also comprises a first acoustic impedance matching layer 18 bonded to the metallized forward face (which forms the ground electrode) of piezoelectric layer 2, as shown in FIG. 1. A second acoustic impedance matching layer 20 is bonded to first acoustic impedance matching layer 18. Layers 2, 18 and 20 in the transducer pallet are bonded using acoustically transparent thin layers of adhesive. The acoustic impedance of second matching layer 20 must be less than the acoustic impedance of first matching layer 18 and greater than the acoustic impedance of the medium acoustically coupled to the transducer array. For example, second matching layer 20 may consist of a plastic material, such as polysulfone or Rexolite, which has excellent acoustic transmission properties. Rexolite is a trademark for a thermoset material produced by cross-linking polystyrene with divinyl benzene, available from C-LEC Plastics, Inc., Beverly, N.J.

FIG. 1 shows a pallet which has been diced into separate transducer elements, each element comprising stacked layers 2, 4, 6, 18 and 20. The undiced pallet is constructed by laminating sheets or plates to form a stack. The pallet is then diced to a sufficient depth to form the respective transducer elements. A dicing saw is used to form parallel element isolations cuts or kerfs 24. Each cut passes completely through the acoustic matching layers 18, 20 and the piezoceramic layer 2, and extends only partially into an acoustic absorbing layer 16. Kerfs 24 are subsequently filled with elastomer or rubber material.

After dicing, the front faces of second acoustic impedance matching layers 20 of the transducer elements are conventionally bonded to the planar rear face of a convex cylindrical lens 22 using an acoustically transparent thin layer of silicone adhesive. Lens 22 serves three purposes: (1) acoustic focusing (due to its lens-shaped cross section and its low acoustic velocity material properties); (2) providing a chemical barrier to protect the transducer elements from attack by gels, body fluids, cleaning agents, etc.; and (3) providing an electrical barrier to protect the patient from the electrically active transducer elements. The lens is conventionally made of silicone rubber.

Figure 2:
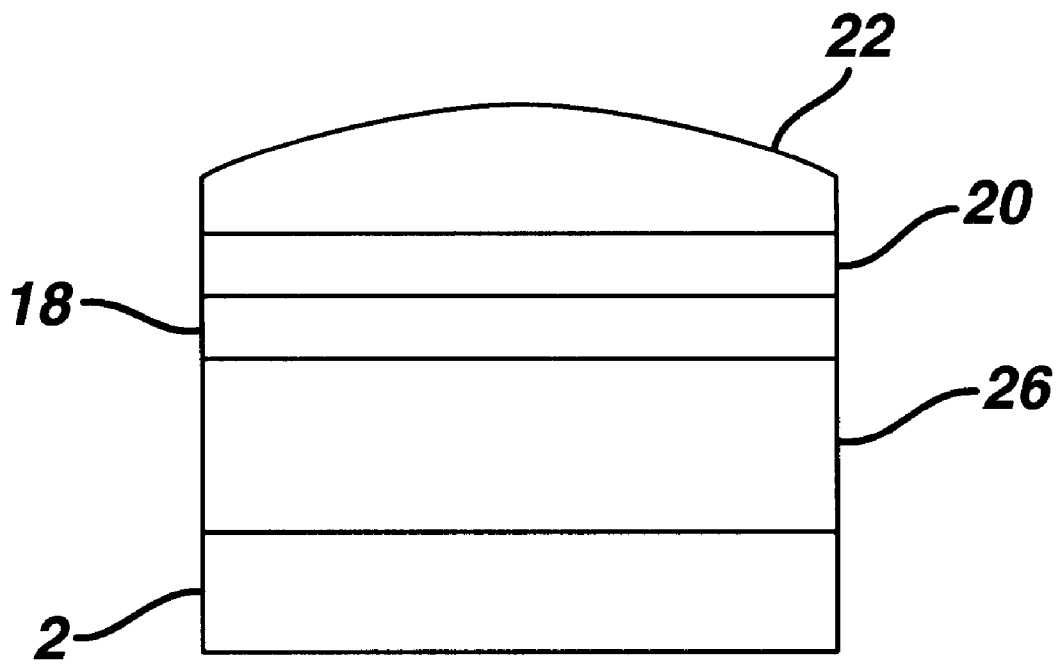
FIG. 2 is a schematic elevation view of part of a transducer pallet in accordance with the preferred embodiments of the invention.

In accordance with a preferred embodiment of the invention, each transducer element comprises three acoustic matching layers. As shown in FIG. 2, each transducer element comprises a first acoustic matching layer 26 of single-crystal silicon bonded to the metallized front face of a layer 2 of piezoelectric material; a second acoustic matching layer 18 of graphite impregnated with metal (e.g., copper, antimony or similar metal) inclusions bonded to first acoustic matching layer 26; and a third acoustic matching layer 20 of Rexolite bonded to second acoustic matching layer 18. Silicon has the advantages of being a simple, readily available and ubiquitous material, which is easily processed and has been extensively studied. Since silicon is the building block for most semiconductor electronics, wafers up to many inches in diameter are readily available.

In the simplest embodiment, a silicon wafer as obtained for semiconductor processing is ground to an appropriate thickness, and included in the acoustic stack with other matching layer materials during transducer construction. The exact thickness is determined by the details of the design, but is nominally a quarter wavelength in the material.

In order to provide a transducer matching layer structure having a Chebyshev bandshape, the ideal acoustic impedance for the third matching layer is about 18.6 Mrayls, so that the standard silicon wafer with an impedance of 19.6 Mrayls is nearly, but not quite, optimum. However different shapes lead to modified values of the acoustic impedance. By changing the shape of the silicon to a narrow beam, for example, which is the appropriate shape for a transducer array element, a better match to the desired impedance is obtained.

In accordance with a further preferred embodiment, the silicon wafer orientation can be selected to more accurately match the acoustic impedance of the silicon to that required for a specific bandshape design. Since silicon is a cubic material, three standard orientations, or "cuts", designated by Miller indices (100), (110) and (111) are available. These indices are related to the orientation of the wafer plane relative to the crystal axes. The respective acoustic impedances for the three cuts are as follows:

| CUT | $Z_{long}$ | $Z_{shear}$ | $Z_{beam}$ |
| --- | --- | --- | --- |
| (100) | 19.6 | 13.6 | 18.1 |
| (110) | 21.3 | 10.9 | 20.9 |
| (111) | 21.7 | 11.6 | 21.2 |

In the above table, $Z_{long}$ and $Z_{shear}$ denote the acoustic impedance for longitudinal and shear waves in bulk material, respectively. Acoustic impedance is a useful concept for describing the transmission and reflection of acoustic waves at the boundary between two materials, and is dependent on material properties such as density and stiffness, as well as the type of acoustic wave and the shape of the material. Additionally, in most ultrasound transducer arrays, the matching layer is not continuous, but is cut into separate beams, and acoustic waves traveling in the thickness dimension therefore have additional constraints imposed by the sides of the beams. $Z_{beam}$ thus denotes the acoustic impedance for a thickness mode vibration in a long narrow bar as commonly used in ultrasound arrays.

As shown in the above table, it is possible to achieve slightly different acoustic impedances and hence optimize the acoustic design. In the final and most complex embodiment, if alternative cuts are taken, even more flexibility in acoustic impedance is possible. As presented in standard crystal physics textbooks [e.g., B. A. Auld, Acoustic Fields and Waves in Solids, Chapter 7, Section 3.D, J. W. Wiley, N.Y., 1973], the elastic constants of silicon are a function of the crystal orientation and are easily calculated. In particular, a computer program can be used to calculate the elastic matrix of a silicon crystal for an arbitrary set of Euler angles using the Bond matrices.

A three-matching-layer Chebyshev design was synthesized using computer models. The main free parameters in the models were the thicknesses of the matching layers. These layers were then fabricated and used in pallet construction. The pallet was then tested. The details and results of this experiment are set forth below.

The piezoelectric material selected was a ceramic that had an acoustic impedance of 32.35 Mrayls and a speed of sound equal to 4,147 m/sec. For the purpose of the computer simulation, the thickness of the piezoceramic layer was fixed at 218 microns. The impedances of the three matching layers were fixed at 19.6, 7.4 and 2.44 Mrayls corresponding to single-crystal silicon (100), SbGr and Rexolite respectively. Rexolite and SbGr (i.e., graphite impregnated with antimony) were chosen because they are used in a known two-matching layer wideband probe design. However, the invention is not limited to use of those materials. Other materials having similar properties can be used for the second and third matching layers. Single-crystal silicon was chosen for the first matching layer because its impedance is close to the optimum value 18.6 Mrayls for a Chebyshev bandshape.

Figure 3:
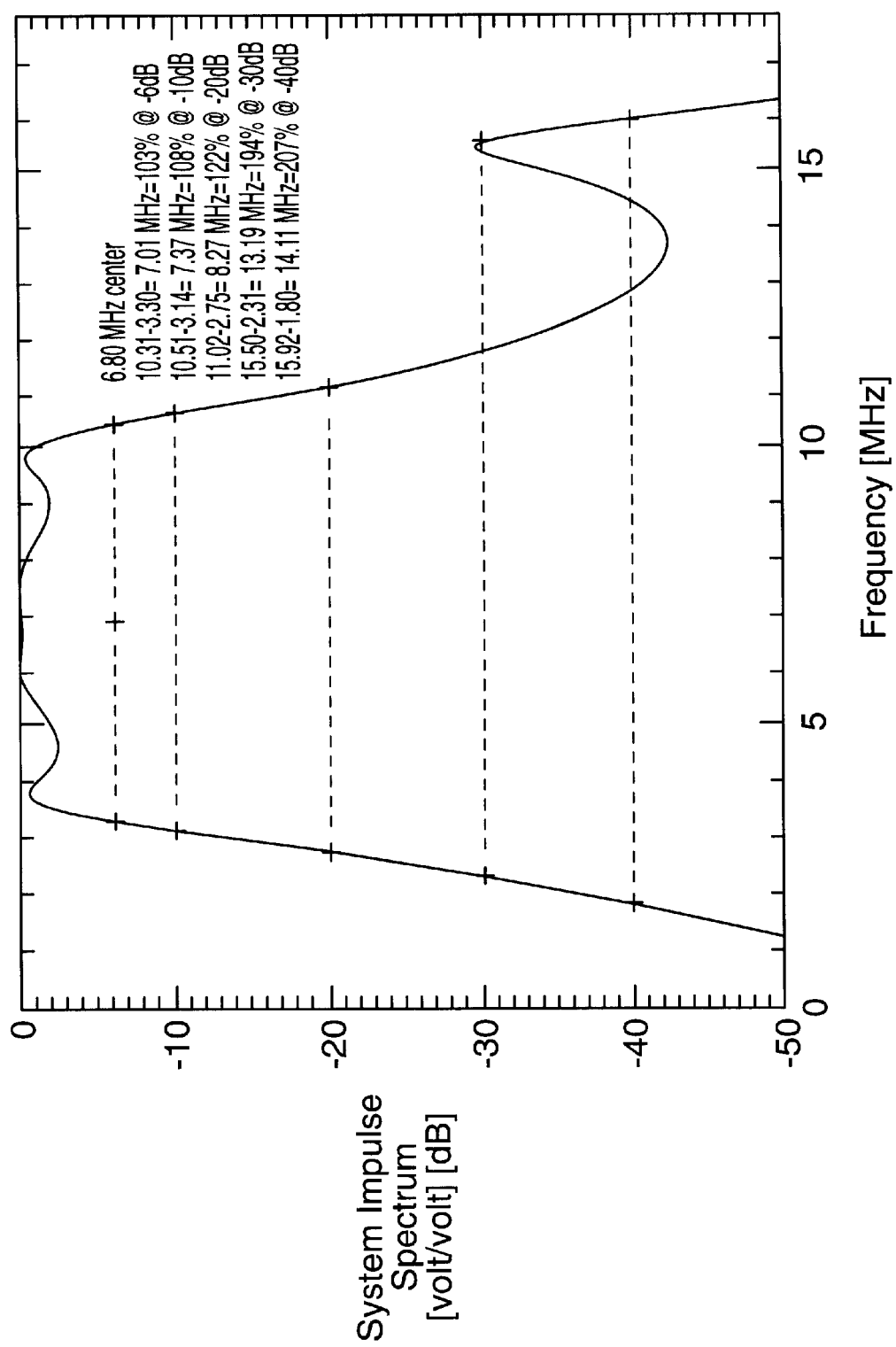
FIG. 3 is a graph of the transfer function for a computer-simulated transducer having a fractional bandwidth of 103% and an almost Chebyshev bandshape.

Both a one-dimensional model (which assumed only one mode of vibration) and a finite-element model (FEM) were used to simulate the acoustic response of a three-matching-layer design using the aforementioned materials. The one-dimensional model was used to optimize thickness of the matching layers. In the one-dimensional optimization, the respective acoustic impedances and velocities (of sound) of the three matching layers were fixed at the following values: $Z_{Si}$=19.60 Mrayls, $v_{Si}$=8,270 m/sec; $Z_{SbGr}$=7.40 Mrayls, $v_{SbGr}$=2,800 m/sec; and $Z_{rexolite}$=2.44 Mrayls, $v_{rexolite}$=2,324 m/sec. Only the thickness of the acoustic matching layers were allowed to vary. The acoustic output energy was then fed into the FEM, which accounted for the aspect ratio and the finite size effects of $Z_{si}$ and $v_{si}$ The parameters from the FEM (finite element model) were then fed back into the one-dimensional model for re-optimization. The design of the transducer was for a 103% fractional bandwidth transducer with an almost Chebyshev shape, having four peaks with the two central ones crowded together to form a single peak. The predicted shape of the transfer function for the optimized design is shown in FIG. 3. The calculated thicknesses of the matching layers for the optimized design were as follows: silicon—313.5 microns; SbGr—104.9 microns; Rexolite—85.83 microns.

A pallet having matching layers and a piezoceramic layer with the foregoing thicknesses was then constructed for testing. P-type (100) silicon wafers were ground to the desired thickness, i.e., 313.5 microns. A 25-micron-wide dicing blade was used, which slightly reduced the active area of the transducer elements.

Test results showed a fractional bandwidth of 95–97%, which is substantially better than the 75% obtained with a standard two-matching layer design using SbGr and Rexolite, and a temporal response comparable to the standard two-matching layer design. Sensitivity was about 2 dB less than the standard two-matching layer design, probably because the ceramic area had been reduced and additional losses were present in the matching layer structure. The two-way transfer function was measured using a standard flat plate reflector. The test data fit the predicted shape of the transfer function shown in FIG. 3 quite closely, with a wide central bump and two peaks at each end of the band. Since only existing matching layer materials were used in this test, improvements can be achieved using a more optimized design. The design theory indicates that fractional bandwidths in the 100% range are attainable. In particular, the matching layer structure can be optimized by varying the orientation of the silicon single-crystal structure in each transducer element.

While most ultrasound transducers currently use a ceramic as the piezoelectric element, advances in piezoelectric single crystal growth, particularly PZNT (lead zinc niobate titanate) and PMNT (lead magnesium niobate titanate) suggest that these materials may become available within the next several years. Use of this material with higher piezoelectric coupling will extend the bandwidth of these devices even more. It will be understood that variation in the acoustic impedance of the piezoelectric will causes changes in the design for the thickness of the layers and hence the orientation of the silicon matching layer cut.

Figure 4:
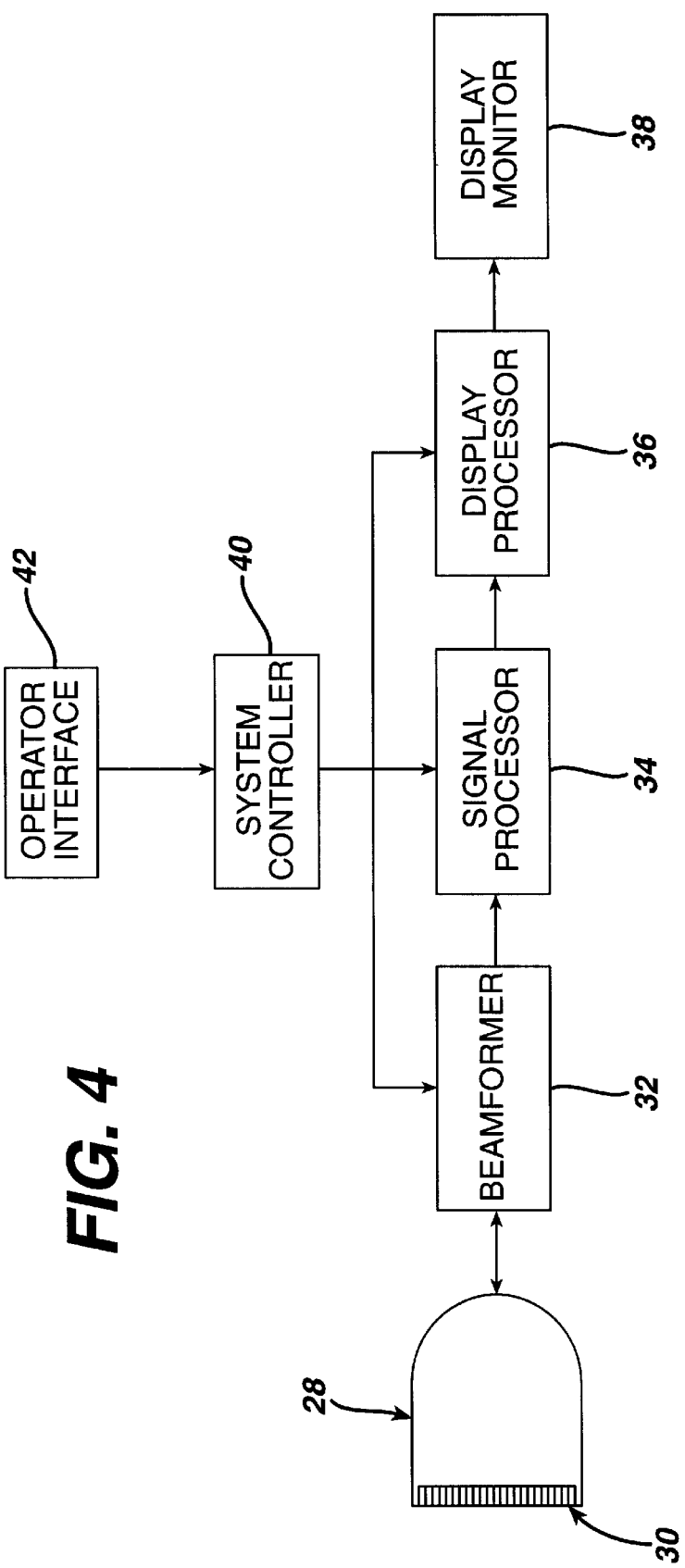
FIG. 4 is a block diagram of a real-time digital ultrasound imaging system in which a transducer of ultra wide bandwidth and having a silicon matching layer can be incorporated.

The ultrasound transducer probe of the invention can be incorporated in an otherwise conventional ultrasound imaging system and has particular application in systems having a harmonic imaging mode. The basic signal processing chain in a B-mode imaging system incorporating the invention and having a harmonic imaging mode is depicted in FIG. 4. An ultrasound probe 28 includes a transducer array 30 comprising a multiplicity of transducer elements, each element comprising a piezoelectric layer and a silicon acoustic matching layer with a ground electrode therebetween. The elements of the transducer array are activated by respective pulsers incorporated in a transmitter portion of a beamformer 32. The pulsers are controlled to cause the transducer array to transmit an ultrasound beam focused at a transmit focal position and having a fundamental center frequency. The return ultrasound wave energy is transduced to electrical RF (radio frequency) signals by the transducer elements. These electrical signals are received in respective receive channels of a receiver portion of beamformer 32. The receive portion of beamformer 32 dynamically focuses the receive signals at successive ranges along a scan line in well-known manner to form a receive vector. The beamformer output data (I/Q or RF) for each scan line are passed through a B-mode signal processor chain 34, which may include, for example, a bandpass filter for passing a band of harmonic signal components centered at a harmonic frequency, envelope detection and logarithmic compression. Alternatively, other harmonic imaging techniques can be used, e.g., Golay-coded excitation on transmit and decoding on receive. The resulting image data are then processed by a display processor 36 for display on a display monitor 38. System control is centered in a host computer or system controller 40, which accepts operator input commands through an operator interface 42 and in turn controls the various subsystems.

While only certain preferred features of the invention have been illustrated and described, many modifications and changes will occur to those skilled in the art. For example, material having acoustic impedance and speed of sound values similar to those of silicon may be used in place of silicon. In addition, the ultra-wide-bandwidth transducer probe disclosed herein is not limited to use in harmonic imaging systems. It is, therefore, to be understood that the appended claims are intended to cover all such modifications and changes as fall within the true spirit of the invention.

What is claimed is:

1. An ultrasound transducer array comprising a multiplicity of elements, each of said elements comprising:
   a layer (2) of piezoelectric material having a first metallized surface;
   a first acoustic matching layer (26) adjacent said first metallized surface of said layer of piezoelectric material, wherein said first acoustic matching layer is comprised of silicon; and
   a second acoustic matching layer (18) adjacent said first acoustic matching layer, wherein said second acoustic matching layer comprises material having an acoustic impedance less than the acoustic impedance of said first acoustic matching layer.

2. The ultrasound transducer array as recited in claim 1, further comprising a second acoustic matching layer adjacent said first acoustic matching layer, wherein said second acoustic matching layer comprises material having an acoustic impedance less than the acoustic impedance of said first acoustic matching layer.

3. The ultrasound transducer array as recited in claim 1, further comprising a third acoustic matching layer (20) adjacent said second acoustic matching layer, said third acoustic matching layer comprising material having an acoustic impedance less than the acoustic impedance of said second acoustic matching layer.

4. The ultrasound transducer array as recited in claim 3, wherein said third acoustic matching layer is comprised of Rexolite.

5. The ultrasound transducer array as recited in claim 3, further comprising an acoustic lens adjacent said third acoustic matching layer.

6. The ultrasound transducer array as recited in claim 1 wherein said piezoelectric material comprises a ceramic.

7. The ultrasound transducer array as recited in claim 6, wherein said ceramic comprises lead zirconate titanate.

8. The ultrasound transducer array as recited in claim 1, wherein said second acoustic matching layer is comprised of antimony-graphite composite material.

9. The ultrasound transducer array as recited in claim 1, wherein said layer of piezoelectric material includes a second metallized surface, and further comprising a mass of acoustic absorbing material adjacent said second metallized surface.

10. The ultrasound transducer array as recited in claim 1, wherein said silicon has a single-crystal structure oriented so that said first acoustic matching layer has an acoustic impedance of about 19.6 Mrayls.

11. A method of manufacturing an ultrasound transducer array, comprising the steps of:
   (a) metallizing a surface of a piezoelectric layer;
   (b) applying a first acoustic matching layer to said metallized surface of said layer of piezoelectric material to form a stack of layers;
   (c) applying a second acoustic matching layer to said first acoustic matching layer so as to enlarge said stack;
   (d) applying a third acoustic matching layer to said second acoustic matching layer so as to further enlarge said stack; and
   (e) dicing said stack to form an array of separate elements, wherein said first acoustic matching layer comprises a silicon wafer, said second acoustic matching layer has an acoustic impedance less than the acoustic impedance of said first acoustic matching layer, and said third acoustic matching layer has an acoustic impedance less than the acoustic impedance of said second acoustic matching layer.

12. The method as recited in claim 11, wherein said silicon wafer has a single-crystal structure oriented to have an impedance close to an optimum value for a Chebyshev bandshape and said first acoustic matching layer has an acoustic impedance of about 19.6 MRayls.

13. An ultrasound transducer array comprising a multiplicity of elements, each of said elements comprising:
   a layer of piezoelectric material having first and second surfaces;
   a first electrode electrically coupled to said first surface of said layer of piezoelectric material; and
   a first acoustic matching layer having first and second surfaces, said second surface of said first acoustic matching layer being acoustically coupled to said first surface of said layer of piezoelectric material;
   wherein said first acoustic matching layer has an acoustic impedance in the range of about 18.6 to 19.6 MRayls and is comprised of a non-composite material.

14. The ultrasound transducer array as recited in claim 13, wherein said first acoustic matching layer comprises silicon.

15. The ultrasound transducer array as recited in claim 14, wherein said silicon has a single-crystal structure oriented to have an impedance close to an optimum value for a Chebyshev bandshape and said first acoustic matching layer has an acoustic impedance of about 19.6 MRayls.

16. The ultrasound transducer array as recited in claim 13, further comprising a second acoustic matching layer having first and second surfaces, said second surface of said second acoustic matching layer being acoustically coupled to said first surface of said first acoustic matching layer.

17. The ultrasound transducer array as recited in claim 16, further comprising a third acoustic matching layer having first and second surfaces, said second surface of said third acoustic matching layer being acoustically coupled to said first surface of said second acoustic matching layer.

18. The ultrasound transducer array as recited in claim 17, wherein said third acoustic matching layer comprises Rexolite.

19. The ultrasound transducer array as recited in claim 17, further comprising an acoustic lens adjacent said third acoustic matching layer of said transducer elements.

20. The ultrasound transducer array as recited in claim 16, wherein said piezoelectric material comprises a ceramic.

21. The ultrasound transducer array as recited in claim 20, wherein said ceramic comprises lead zirconate titanate.

22. The ultrasound transducer array as recited in claim 16, wherein said second acoustic matching layer comprises antimony-graphite composite materials.

23. The ultrasound transducer array as recited in claim 13, further comprising:
   a second electrode electrically coupled to said second surface of said layer of piezoelectric material; and
   a mass of acoustic absorbing material acoustically coupled to said second surface of said layer of piezoelectric material.

24. A method of transmitting ultrasound we energy into human tissue, comprising the steps of:
   electrically activating a layer (2) of piezoelectric ceramic material to generate ultrasound wave energy; and passing said ultrasound wave energy through a first acoustic matching layer (26) adjacent to a metallized surface of said layer of piezoelectric material, wherein said first acoustic matching layer is comprised of silicon; and passing said ultrasound wave energy through a second acoustic matching layer (18) adjacent said first acoustic matching layer, wherein said second acoustic matching layer comprises material having an acoustic impedance less than the acoustic impedance of said first acoustic matching layer.

25. An ultrasound imaging system comprising:

an array (30) of transducer elements;

a beamformer (32) including a multiplicity of pursers (12) for activating said transmitter elements to transmit ultrasound wave energy and further including a multiplicity of receive channels for receiving electrical receive signals from said transducer elements generated in response to ultrasound wave energy returning to said transducer elements;

a signal processor (34) for processing said receive signals to form image data; and a display subsystem (36, 38) for displaying an image which is a function of said image data, wherein each of said transducer elements comprises:

a layer (2) of piezoelectric ceramic material having first and second surfaces;

an electrode (6) electrically coupled to said first surface of said layer of piezoelectric material;

a first acoustic matching layer (26) having first and second surfaces said second surface of said first acoustic matching layer being acoustically coupled to said first surface of said layer of piezoelectric ceramic material, wherein said acoustic matching layer is comprised of silicon; and a second acoustic matching layer (18) adjacent said first acoustic matching layer, wherein said second acoustic matching layer comprises material having an acoustic impedance less than the acoustic impedance of said first acoustic matching layer.

* * * * *